United States Patent [19]
Tropsch et al.

[11] Patent Number: 5,869,032
[45] Date of Patent: Feb. 9, 1999

[54] QUATERNIZED COPOLYMERS SUITABLE AS ACTIVE INGREDIENTS IN COSMETIC FORMULATIONS, SUCH AS HAIR STYLING COMPOSITIONS

[75] Inventors: Jürgen Tropsch, Römerberg; Axel Sanner, Frankenthal; Peter Hössel, Schifferstadt; Hans-Jürgen Raubenheimer, Ketsch; Christian Schade, Ludwigshafen, all of Germany

[73] Assignee: BASF Aktiengesellschaft, Ludwigshafen, Germany

[21] Appl. No.: 824,920

[22] Filed: Mar. 27, 1997

Related U.S. Application Data

[63] Continuation of Ser. No. 567,515, Dec. 5, 1995, abandoned.

[30] Foreign Application Priority Data

Dec. 7, 1994 [DE] Germany .......................... 44 43 568.1

[51] Int. Cl.$^6$ ............................... A61K 7/06; A61K 7/48; C08F 226/10
[52] U.S. Cl. ...................... 424/70.15; 424/47; 424/78.03; 424/78.22; 424/78.24; 424/78.32; 526/263; 526/264; 525/326.9

[58] Field of Search ...................... 526/263, 264; 525/326.9; 424/47, 70.15, 78.03, 78.22, 78.24, 78.32

[56] References Cited

U.S. PATENT DOCUMENTS

| 3,313,734 | 4/1967 | Lang . |
| 5,506,315 | 4/1996 | Meyer ...................................... 526/264 |

FOREIGN PATENT DOCUMENTS

| 2040963 | 10/1991 | Canada . |
| 544 158 | 6/1993 | European Pat. Off. . |
| 455 081 | 6/1994 | European Pat. Off. . |
| 4138763 | 5/1993 | Germany . |
| 94/02115 | 2/1994 | WIPO . |

OTHER PUBLICATIONS

Derwent Abstract 95–276979/37 (of FR 2715841).

*Primary Examiner*—David Butner
*Attorney, Agent, or Firm*—Keil & Weinkauf

[57] ABSTRACT

Quaternized copolymers suitable as active ingredients in hair styling compositions are obtainable from N-vinylimidazoles, N-vinylcaprolactam, N-vinylpyrrolidone and, if required, further monomers.

13 Claims, No Drawings

QUATERNIZED COPOLYMERS SUITABLE AS ACTIVE INGREDIENTS IN COSMETIC FORMULATIONS, SUCH AS HAIR STYLING COMPOSITIONS

This application is a continuation of application Ser. No. 08/567,515, filed on Dec. 5, 1995 now abandoned.

The present invention relates to polymers obtainable by free radical copolymerization of monomer mixtures comprising (a) from 5 to 50% by weight of a 1-vinylimidazole or of a quaternized 1-vinylimidazole, (b) from 20 to 80% by weight of N-vinylcaprolactam, (c) from 10 to 60% by weight of N-vinylpyrrolidone and (d) from 0 to 30% by weight of a further monomer which is capable of free radical copolymerization and, as a homopolymer, has a glass transition temperature of more than 20° C., and, if an unquaternized 1-vinylimidazole is used as monomer (a), subsequent quaternization of the polymer.

The present invention furthermore relates to the use of such polymers as active ingredients in cosmetic formulations, preferably in cosmetic hair formulations, especially in hair styling compositions having care properties, and cosmetic hair formulations containing such polymers as active ingredient, in particular cosmetic hair formulations in the form of foams.

After application, hair styling compositions should impart pronounced and permanent curl retention to the hairstyle and furthermore give rise to a good hair sensation (good feel, good body and low hair tack) and should prevent the build up of static charge and have a conditioning action, ie. should have a beneficial effect on the wet combability of the hair.

This large number of requirements has been met to date only by the combination of anionic or neutral hair setting polymers with cationic or silicone-containing conditioners or conditioner polymers.

WO 94/02115 describes hair styling compositions in the form of foams which are said to have a simultaneous setting and conditioning action and therefore consist of a mixture of a setting polymer, a polycationic, conditioning polymer and surfactants.

EP-A 544 158 discloses the use of homo- or copolymers based on quaternized 1-vinylimidazoles as organic polyelectrolytes in cosmetic formulations.

Furthermore, EP-A 455 081 discloses unquaternized copolymers of 1-vinylimidazole, N-vinylcaprolactam and N-vinylpyrrolidone, which are particularly suitable for use in hair setting compositions.

It is an object of the present invention to provide improved polymers which, when used in hair styling compositions, simultaneously have setting and care properties.

We have found that this object is achieved by the polymers defined at the outset, the use thereof and cosmetic hair formulations containing such polymers.

The novel copolymers are obtainable by free radical copolymerization of monomer mixtures comprising (a) from 5 to 50, preferably from 7 to 20, % by weight of an N-vinylimidazole or of a quaternized N-vinylimidazole, (b) from 20 to 80, preferably from 40 to 60, % by weight of N-vinylcaprolactam, (c) from 10 to 60, preferably from 20 to 50, % by weight of N-vinylpyrrolidone and (d) from 0 to 30, preferably from 0 to 15, % by weight of a further monomer which is capable of free radical copolymerization and, as a homopolymer, has a glass transition temperature of more than 20° C., and, if an unquaternized N-vinylimidazole is used as monomer (a), subsequent quaternization of the polymer.

Suitable N-vinylimidazoles (monomers (a)) are 1-vinylimidazole derivatives of the general formula I

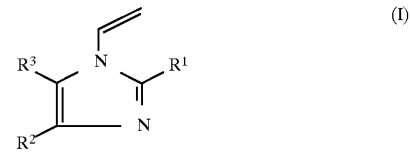

where $R^1$ is hydrogen, $C_1$–$C_4$-alkyl or phenyl and $R^2$ and $R^3$ may be identical or different and are each hydrogen or $C_1$–$C_4$-alkyl.

The vinylimidazoles may be used as free bases or in quaternized form, the copolymerization of quaternized vinylimidazoles being preferred. If the vinylimidazoles are used in the copolymerization in the form of the free bases, quaternization is effected after the polymerization.

For example, alkyl halides of 1 to 22 carbon atoms in the alkyl group, eg. methyl chloride, methyl bromide, methyl iodide, ethyl chloride, ethyl bromide, propyl chloride, hexyl chloride, dodecyl chloride and lauryl chloride, and benzyl halides, in particular benzyl chloride and benzyl bromide, are suitable for quaternizing the vinylimidazole. Further suitable quaternizing agents are dialkyl sulfates, in particular dimethyl sulfate or diethyl sulfate. The quaternization of the vinylimidazoles may also be carried out with alkylene oxides, such as ethylene oxide or propylene oxide, in the presence of acids. Preferred quaternizing agents are methyl chloride, dimethyl sulfate or diethyl sulfate. Very particular preferred monomers of group (a) are 3-methyl-1-vinylimidazolium chloride and methylsulfate. The quaternization of the monomers or of a polymer with one of the stated quaternizing agents can be carried out by a generally known method.

Examples of suitable monomers (d) are $C_1$–$C_{12}$-alkyl esters of acrylic acid or of methacrylic acid, such as tert-butyl acrylate, isobutyl methacrylate, n-butyl methacrylate, methyl methacrylate, ethyl methacrylate, tert-butyl methacrylate, isobornyl acrylate or isobornyl methacrylate, or acrylamides, such as N-tert-butyl-acrylamide or N-tert-octylacrylamide. Other suitable monomers which have a water solubility of more than 5% by weight at 25° C. are for example, acrylic acid, methacrylic acid, crotonic acid, N-methylolmethacrylamide, N-vinyl-N-methylacetamide, N-vinylformamide, acrylamide, N,N-dimethylacrylamide, methacrylamide, N-vinyloxazolidone, N-vinyltriazole, hydroxyalkyl (meth)acrylates or alkylethylene glycol (meth) acrylates having 1–50 ethylene glycol units in the molecule.

Copolymers of (a) from 10 to 30% by weight of 3-methyl-1-vinylimidazolium methylsulfate, (b) from 40 to 60% by weight of N-vinylcaprolactam and (c) from 30 to 50% by weight of N-vinylpyrrolidone are very particularly preferred.

The polymers can be prepared by the conventional free radical polymerization method. The preparation is preferably carried out as a solution polymerization in a solvent such as water, methanol, ethanol, isopropanol or a mixture of these solvents. The amounts of monomers and solvents are advantageously chosen so that 15–60% strength by weight solutions form. The polymerization is usually carried out at from 60° to 130° C. and at atmospheric or autogenous pressure.

The initiators used for the free radical polymerization may be the peroxo and/or azo compounds usually used for this purpose, for example dibenzoyl peroxide, tert-butyl perpivalate, tert-butyl 2-ethylhexanoate, di-tert-butyl peroxide, tert-butyl hydroperoxide, azobisisobutyronitrile, azobis(2-amidinopropane) dihydrochloride or 2,2'-azobis(2-methylbutyronitrile). Initiator mixtures or conventional redox initiators are also suitable. The initiators can be used in the usual amounts, for example from 0.05 to 5% by weight, based on the amount of the monomers to be polymerized.

If desired, the molecular weight can be regulated by adding regulators, for example compounds which contain sulfur in bound form.

The K values of the polymers should be from 10 to 350, preferably from 50 to 300. The K value desired in each case can be established in a manner known per se, by the choice of the polymerization conditions, for example of the duration of polymerization, the initiator concentration and the regulator concentration. The K values are measured according to Fikentscher, Cellulosechemie, 13 (1932), 58–64, at 25° C. in 0.1% strength by weight aqueous solution.

The novel polymers are suitable for use as active ingredients in cosmetic formulations, either skin cosmetics in formulations, such as liquid soaps, body lotions, aftershaves, face lotions and other cosmetic lotions or in particular cosmetic hair formulations, such as hair repair treatments, hair lotions, hair rinses, hair emulsions, damaged-end fluids, neutralizing compositions for permanent waves, hot oil treatment products, conditioners, setting lotions or hair sprays. Depending on the application, the cosmetic hair formulations may be applied as spray, foam, gel, gel spray or mousse.

In addition to the novel polymers and suitable solvents, such as water or water/alcohol mixtures, the cosmetic hair formulations may also contain additives conventionally used in cosmetics, such as emulsifiers, preservatives, perfume oils, care ingredients, such as panthenol, collagen, vitamins, protein hydrolysis products, stabilizers, pH regulators, colors and other conventional additives.

The novel polymers are particularly suitable for use in hair styling compositions having care properties. Such hair styling compositions can preferably be used in the form of foams, such as aerosol hair foams or pump foams, or as hair gels.

Novel hair styling compositions are preferably used in the form of foams. Such formulations suitable for foams may also contain the additives conventionally used in cosmetics and the usual additives in addition to the polymers and water or water/alcohol mixtures as solvents. Where the hair styling compositions are used as aerosol foams, they contain conventional propellants, such as mixtures of propane/butane, dimethyl ether or compressed air. If the hair styling compositions are to be used as pump foams, the addition of propellants is unnecessary; in this case, application is effected by means of the apparatuses usually used for this purpose.

A formulation suitable according to the invention for the aerosol foams may have, for example, the following composition:
(a1) from 0.01 to 10% by weight of a novel polymer,
(a2) from 5 to 20% by weight of a propellant, for example propane/butane,
(a3) from 0.1 to 5% by weight of an emulsifier, for example cetyldimethyl-2-hydroxyethylammonium dihydrogen phosphate or Cetheareth-25 (CTFA),
(a4) from 0.1 to 20% by weight of conventional cosmetic assistants and
(a5) water or a water/alcohol mixture to 100% by weight.

A formulation suitable for pump foams may have a similar composition but contain no propellant (a2).

Cosmetic hair formulations which are to be used in the form of gels also contain gel-forming substances, for example carbomers (CTFA).

The novel polymers may also be mixed with conventional polymers for hair cosmetics if very special properties are to be established.

Examples of suitable conventional polymers for hair cosmetics are anionic polymers. Such anionic polymers are homo- and copolymers of acrylic or methacrylic acid or salts thereof, copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of tert-butyl acrylate, ethyl acrylate and methacrylic acid (eg. Luvimer® 100P), copolymers of N-tert-butylacrylamide, ethyl acrylate and acrylic acid (Ultrahold® 8, strong), copolymers of vinyl acetate, crotonic acid and vinyl propionate (eg. Luviset® CAP), maleic anhydride copolymers, if required reacted with alcohols, or anionic polysiloxanes, for example copolymers having carboxyl functional groups and comprising vinylpyrrolidone, tert-butyl acrylate and methacrylic acid (eg. Luviskol® VBM).

Very particularly preferred anionic polymers are acrylates having an acid number greater than or equal to 120 and copolymers of tert-butyl acrylate, ethyl acrylate and methacrylic acid.

Further suitable polymers for hair cosmetics are cationic polymers, such as Polyquaternium 1 to x according to INCI, copolymers of vinylpyrrolidone/vinylimidazolium salts (Luviquat® FC, Luviquat® HM), copolymers of vinylpyrrolidone/dimethylaminoethyl methacrylate, quaternized with diethyl sulfate (Luviquat® PO 11); cationic cellulose derivatives (Polyquaternium 4 and 10) and acrylamide copolymers (Polyquaternium 7). Particularly suitable cationic polymers are copolymers of vinylpyrrolidone/vinylimidazolium chloride 5:95 (Luviquat® FC 905).

Further suitable polymers for hair cosmetics are neutral polymers, such as polyvinylpyrrolidone, copolymers of vinylpyrrolidone and vinyl acetate and/or vinyl propionate, polysiloxanes, polyvinylcaprolactam and copolymers with vinylpyrrolidone, polyethyleneimines and salts thereof, polyvinylamines and salts thereof, cellulose derivatives, polyaspartic acid salts and derivatives. A preferred neutral polymer is polyvinylcaprolactam.

To obtain certain properties, the formulations may additionally contain conditioning substances based on silicone compounds. Suitable silicone compounds are, for example, polyalkylsiloxanes, polyarylsiloxanes, polyarylalkylsiloxanes, polyethersiloxanes or silicone resins.

Cosmetic hair formulations, in particular hair styling compositions, which contain the novel polymers as sole active ingredients have good setting properties as well as good care properties. Hair treated with such compositions imparts a pleasant skin sensation, is nontacky and readily combable and does not have a static charge. The good film formation properties of the polymers make them readily distributable over the hair.

Preparation of the copolymers 300 g of water were initially taken in a stirred apparatus having an attached reflux condenser and were heated to 65° C. while stirring in a stream of nitrogen. After this temperature had been reached, the monomer mixture (for composition, see Table 1) in 250 g of water was added in the course of 4 hours and a feed comprising 2 g of 2,2'-azobis (2-amidinopropane) dihydrochloride in 50 g of water was added in the course of 5 hours. The mixture was then stirred for a further two hours at this temperature. A clear solution of a polymer was obtained.

TABLE 1

| Ex. | Monomer (a) | N-Vinyl-caprolac-tam (b) | N-Vinyl-pyrrolid-one (c) | Monomer (d) | K value |
|---|---|---|---|---|---|
| 1 | 3-Ethyl-1-vinylimidazolium methylsulfate 80 g | 162 g | 162 g | — | 242 |
| 2 | 3-Methyl-1-vinylimidazolium chloride 40 g | 200 g | 160 g | — | 245 |
| 3 | 3-Methyl-1-vinylimidazolium methylsulfate 40 g | 320 g | 40 g | — | 233 |
| 4 | 3-Methyl-1-vinylimidazolium methylsulfate 40 g | 180 g | 160 g | tert-Butyl acrylate 20 g | 236 |
| 5 | 3-Methyl-1-vinylimidazolium methylsulfate 40 g | 300 g | 40 g | tert-Butyl acrylate 20 g | 212 |
| 6 | 3-Methyl-1-vinylimidazolium methylsulfate 40 g | 200 g | 160 g | — | 275 |
| 7 | 3-Methyl-1-vinylimidazolium methylsulfate 120 g | 120 g | 160 g | — | 256 |

Preparation of cosmetic hair formulations

Formulation 1:

| 03.00 g | of polymer according to Example 3 |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane |
| to 100.00 g | of water |

Formulation 2:

| 03.00 g | of polymer according to Example 4 |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

Formulation 3:

| 03.00 g | of polymer according to Example 5 |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

Formulation 4:

| 03.00 g | of polymer according to Example 2 |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

TABLE 1-continued

Formulation 5:

| 03.00 g | of polymer according to Example 6 |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

Formulation 6 (comparative example):

| 03.00 g | of a polymer of 50% by weight of N-vinylprrolidine and 50% by weight of N-vinylimidazolium chloride |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

Formulation 7 (comparative example):

| 01.00 g | of polymer (7a) of 50% by weight of N-vinyl-prrolidine/50% by weight of N-vinylimidazolium chloride |
| 02.00 g | of polymer (7b) of 60% by weight of N-vinyl-pyrrolidone/40% by weight of vinyl acetate |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

Formulation 8 (comparative example):

| 01.20 g | of polymer (7a) |
| 03.30 g | of polymer (7b) |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

Formulation 9 (comparative example):

| 01.00 g | of polyquaternium-11 (CTFA) |
| 02.00 g | of polymer (7b) |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane |
| to 100.00 g | of water |

Formulation 10 (comparative example)

| 01.20 g | of polyquaternium-11 (CTFA) |
| 03.30 g | of polymer (7b) |
| 00.10 g | of preservative |
| 00.40 g | of perfume oil*) |
| 00.50 g | of cetyldimethyl-2-hydroxyethylammonium dihydrogen phosphate |
| 10.00 g | of propane/butane (1/3) |
| to 100.00 g | of water |

*)Perfume oil as a mixture with PEG-40/hydrogen sulfated castor oil (CTFA) in a weight ratio of 1:3

Evaluation of setting on a model head at 65% relative humidity 300 g of foam were prepared. A model head comprising Central European hair was washed twice with a 14% strength by weight aqueous solution of sodium lauryl ether sulfate. The hair was parted with a comb. An amount of a novel foam roughly the size of a tennis ball was applied in each case to one half of the head and distributed uniformly. A foam according to a comparative example was applied to the other half of the head in each case.

A second head was treated with the two sides being interchanged. Using separate combs, the wet combability of the model head and the ease of distribution of the foam on the hair were then evaluated by at least two persons (see below). The heads were dried at room temperature overnight.

On the next day, at least two persons evaluated the setting, the tack and the static charge of the heads. The evaluations were based on the rating scale shown in Table 2.

TABLE 2

| Evaluations: | Rating 1 | Rating 2 | Rating 3 |
|---|---|---|---|
| Wet combability | very good | good | poor |
| Ease of distribution | very good | good | poor |
| Setting | very good | good | weak |
| Tack | none | weak | strong |
| Charge buildup | none | weak | strong |

TABLE 3

Evaluation of the setting

| Results of the tests on the halves of the head (ratings) | Formulation 1 | Formulation 2 | Formulation 3 | Formulation 4 | Formulation 5 |
|---|---|---|---|---|---|
| Wet combability | 1 | 1 | 1 | 1 | 1 |
| Ease of distribution | 1 | 1 | 1 | 1 | 1 |
| Setting | 1 | 1 | 1 | 1 | 1 |
| Tack | 1 | 1 | 1 | 1 | 1 |
| Charge buildup | 1 | 1 | 1 | 1 | 1 |

| Results of the tests on the halves of the head (ratings) | Formulation 6 | Formulation 7 | Formulation 8 | Formulation 9 | Formulation 10 |
|---|---|---|---|---|---|
| Wet combability | 1 | 2 | 1 | 1 | 1 |
| Ease of distribution | 1 | 1 | 2 | 1 | 1 |
| Setting | 3 | 3 | 2 | 2 | 2 |
| Tack | 3 | 2 | 3 | 2 | 3 |
| Charge buildup | 1 | 2 | 1 | 1 | 1 |

Determination of curl retention (after application from hair foam solution at 75% relative humidity Formulations 1 to 5 without propane/butane 180 g of this solution were prepared. Strands of medium-brown European human hair weighing 2 g and having a length 15.5 cm were used for determining the curl retention.

Method of determination

The hair strands were stored for 1 hour in a 1:1 ethanol/water solution, rinsed with water and then washed twice with an aqueous Texapon NSO solution (about 0.5% of active ingredient). The hair strands were then rinsed with water at about 40° C. until soap formation was no longer detectable, and were combed and stored in water.

The moist hairs were then immersed three times in the polymer solution (see above), rubbed off with the fingers from time to time and pressed out between filter papers. The hair was then wound round a Teflon rod (12 mm diameter) and fastened with filter paper and a rubber ring. The hair strands were then dried for 90 minutes at 70° C. in a drying oven. After cooling to room temperature, the wiped off curls were suspended on a Plexiglas frame specially produced for this purpose, and the curl length (L0) was measured on the mounted scale. 10 curls were used for determining a curl retention value. The curls were placed in a climatic chamber at 20° C. and 75% relative humidity. Their lengths (Lt) were measured after 5 hours.

The curl retention is calculated as follows:

$$\text{Curl retention in \%} = \frac{L - Lt}{L - L0} \cdot 100$$

L=length of the hairs (15.5 cm)

L0=length of the curl after drying

Lt=length of the curl after treatment in the climatic chamber

The mean value of the 10 individual measurements after 5 hours at 20° C. and 75% relative humidity is stated as the curl retention. The results are listed in Table 4.

TABLE 4

| | Fomulations | | | | | | | | | |
|---|---|---|---|---|---|---|---|---|---|---|
| | 1 | 2 | 3 | 4 | 5 | 6 | 7 | 8 | 9 | 10 |
| Curl retention (%) | 90 | 84 | 98 | 87 | 87 | 39 | 35 | 35 | 43 | 45 |

Determination of tack

The polymers to be tested, in the form of a 20% strength by weight aqueous solution, were applied to a glass sheet using a knife coater having a 120 μm slot width. The wet film was stored overnight in a climatic chamber at 75% relative humidity and 20° C.

A plastic carbon ribbon (Pelikan 2060, 50 mm wide) was placed on the polymer-coated glass sheet. A load of 250N was applied for 10 seconds by means of a rubber stamp having a Shore A hardness of 60±5. The test was carried out in the climatic chamber at 75% relative humidity. The printing ink of the carbon ribbon remains adhering to the polymer film to the extent to which the polymer surface is tacky (evaluation: ratings from 0=nontacky to 5=very highly tacky, >5; polymer film is torn from the glass sheet).

| | Polymer or polymer mixture from formulation | | | | | | | | | |
|---|---|---|---|---|---|---|---|---|---|---|
| | 1 | 2 | 3 | 4 | 5 | 6 | 7 | 8 | 9 | 10 |
| Tack (rating) | 0–1 | 1 | 0 | 2 | 1–2 | >5 | >5 | >5 | >5 | >5 |

EXAMPLES 8 TO 12

In the following examples, blends of polymers are formulated as hair foams. The composition of the foams and the properties are shown in Table 5.

TABLE 5

Hair foams
All formulation examples contain 10% by weight of propane/butane;
0.4% by weight of perfume oil Carina/Cremophor RH40; 0.1% by weight of Euxyl K 100

| Polymers/Example No.<br>Data in % by weight | 8 | 9 | 10 | 11 | 12 |
|---|---|---|---|---|---|
| Copolymer of vinylcaprolactam, vinylpyrrolidone and vinylimidazolium methylsulfate 5:4:1 parts by weight | 2 | 2 | 1 | 2 | 2 |
| Polyvinylcaprolactam | 1 | — | — | — | — |
| Copolymer of methacrylic acid, ethyl acrylate and tert-butyl acrylat, 100% neutralized with aminomethylpropanol (Luvimer 100 P) | — | 1 | 0.5 | — | — |
| Polyquaternium 16 with 95% by weight of vinylimidazolium chloride (Luviquat FC 905) | — | — | — | 0.5 | 0.5 |
| Cremophor A 25 | 0.1 | 0.1 | 0.1 | — | 0.1 |
| Luviquat Mono CP | — | — | — | 0.4 | — |
| Polyquaternium 11 | — | — | — | — | — |
| Flexural strength (cN) | 135 | 345 | 150 | 94 | 95 |
| Tack (Ratings 1 to 5) | 1 | 1 | 1–2 | 3 | 3 |
| Half-head test (Ratings 1 = very good to 3): | | | | | |
| Wet combability | 2–3 | 2 | 2–3 | 1 | 1 |
| Setting | 1–2 | 1 | 2 | 2 | 2–3 |
| Gloss of dry hair | 1 | 2 | 1–2 | 1–2 | 1–2 |

We claim:

1. A polymer suitable for use in hair styling compositions, said polymer being obtained by free radical copolymerization of a monomer mixture comprising
   (a) from 7 to 20% bu weight of a 1-vinylimidazole or of a quaternized 1-vinylimidazole,
   (b) from 40 to 60% by weight of N-vinylcaprolactam,
   (c) from 20 to 50% by weight of N-vinylpyrrolidone and
   (d) from 0 to 15% by weight of a further monomer which is capable of free radical copolymerization and, as a homopolymer, has a glass transition temperature of more than 20° C., which further monomer is selected from the group consisting of $C_1$–$C_{12}$-alkyl esters of acrylic or methacrylic acid, acrylamides,
and methacrylamides, and, if an unquaternized 1-vinylimidazole is used as monomer (a), subsequent quaternization of the polymer.

2. A polymer as defined in claim 1, containing 3-methyl-1-vinylimidazolium chloride or methylsulfate as monomer (a).

3. A polymer as defined in claim 1, containing 3-ethyl-1-vinylimidazolium ethylsulfate as monomer (a).

4. A polymer as defined in claim 1, containing tert-butyl acrylate as monomer (d).

5. A cosmetic hair formulation containing a polymer as defined in claim 1 as an active ingredient.

6. A cosmetic hair formulation as defined in claim 5, in the form of an aerosol foam.

7. A cosmetic hair formulation as defined in claim 5, in the form of a pump foam.

8. A cosmetic hair formulation as defined in claim 5, in the form of a gel.

9. A cosmetic hair formulation as defined in claim 5, containing, in addition to the polymer as an active ingredient, further polymers conventionally used in hair cosmetics.

10. A cosmetic hair formulation as defined in claim 5, containing the assistants conventionally used in hair cosmetics.

11. A cosmetic skin formulation containing a polymer as defined in claim 1 as an active ingredient.

12. A polymer as defined in claim 1 obtained by copolymerization of a monomer mixture comprising
   (a) from 7 to 20% by weight of a 1-vinylimidazole quaternized with dimethyl sulfate or dimethyl sulfate,
   (b) from 40 to 60% by weight of N-vinylcaprolactam and
   (c) from 20 to 50% by weight of N-vinylpyrrolidone.

13. A polymer suitable for use in hair styling compositions, said polymer being obtained by free radical copolymerization of a monomer mixture comprising
   (a) from 5 to 10% by weight of a 1-vinylimidazole or of a quaternized 1-vinylimidazole,
   (b) from 45 to 80% by weight of N-vinylcaprolactam,
   (c) from 20 to 50% by weight of N-vinylpyrrolidone and
   (d) from 1 to 5% by weight of a further monomer which is capable of free radical copolymerization and, as a homopolymer, has a glass transition temperature of more than 20° C.

and, if an unquaternized 1-vinylimidazole is used as monomer (a), subsequent quaternization of the polymer.

* * * * *